United States Patent [19]
Ehlers

[11] Patent Number: 6,151,535
[45] Date of Patent: Nov. 21, 2000

[54] LABORATORY PRIMARY SAMPLE DISTRIBUTOR WITH ARCHIVING MODE

[75] Inventor: Dirk H. Ehlers, Hamburg, Germany

[73] Assignee: Olympus Diagnostica GmbH, Hamburg, Germany

[21] Appl. No.: 09/302,275

[22] Filed: Apr. 30, 1999

[30] Foreign Application Priority Data

May 4, 1998 [DE] Germany .......................... 198 19 813

[51] Int. Cl.$^7$ ...................................................... G06F 7/06
[52] U.S. Cl. ........................... 700/226; 198/340; 422/67; 414/270; 414/331.03; 209/584
[58] Field of Search ............... 198/340; 209/569, 209/583, 584; 414/273, 331.03, 331.05, 269, 270; 700/226; 422/67

[56] References Cited

U.S. PATENT DOCUMENTS

| | | | |
|---|---|---|---|
| 4,679,149 | 7/1987 | Merz | 414/273 X |
| 4,692,308 | 9/1987 | Riley et al. | 422/56 |
| 5,150,795 | 9/1992 | Nakayama et al. | 209/569 |
| 5,346,072 | 9/1994 | Dian et al. | 209/584 |
| 5,390,868 | 2/1995 | Kiriake | 198/340 X |
| 5,601,395 | 2/1997 | Lichti, Sr. et al. | 414/273 X |
| 5,614,415 | 3/1997 | Markin | 422/65 X |
| 5,623,415 | 4/1997 | O'Bryan et al. | 422/65 X |
| 5,943,841 | 8/1999 | Wunscher | 414/273 X |
| 5,972,295 | 10/1999 | Hanawa et al. | 422/65 |
| 6,011,998 | 1/2000 | Lichti et al. | 414/273 X |

FOREIGN PATENT DOCUMENTS 296 08 120 U  9/1996  Germany .

OTHER PUBLICATIONS

Ito Teruaki, Method for Centrifugal Separation Treatment of Specimen and Apparatus Therefor, Patent Abstracts of Japan Pub. No. 07236838 A, publication date Sep. 12, 1995, Appl. No. 06029799 filed Feb. 28, 1994, one page.

*Primary Examiner*—Robert P. Olszewski
*Assistant Examiner*—Thuy V. Tran
*Attorney, Agent, or Firm*—Pearne & Gordon LLP

[57] ABSTRACT

A laboratory primary sample distributor has a source zone for the input of coded receptacles containing samples and delivered in input magazines. In a distribution mode under the control of a control unit, a conveyor belt moves the receptacles from the source zone through a reading system which reads the receptacle codes in a destination zone wherein there are destination transport means. A transfer device transfers the receptacles onto the conveyor belt and a sorter device removes the receptacles from the conveyor belt and deposits them into the destination transport means. The control unit also has an archive mode during which the conveyor belt runs backward relative to the distribution mode, the sorter device transfers receptacles from the destination transport means onto the conveyor belt and the transfer device transfers receptacles from the conveyor belt into archive magazines.

2 Claims, 1 Drawing Sheet

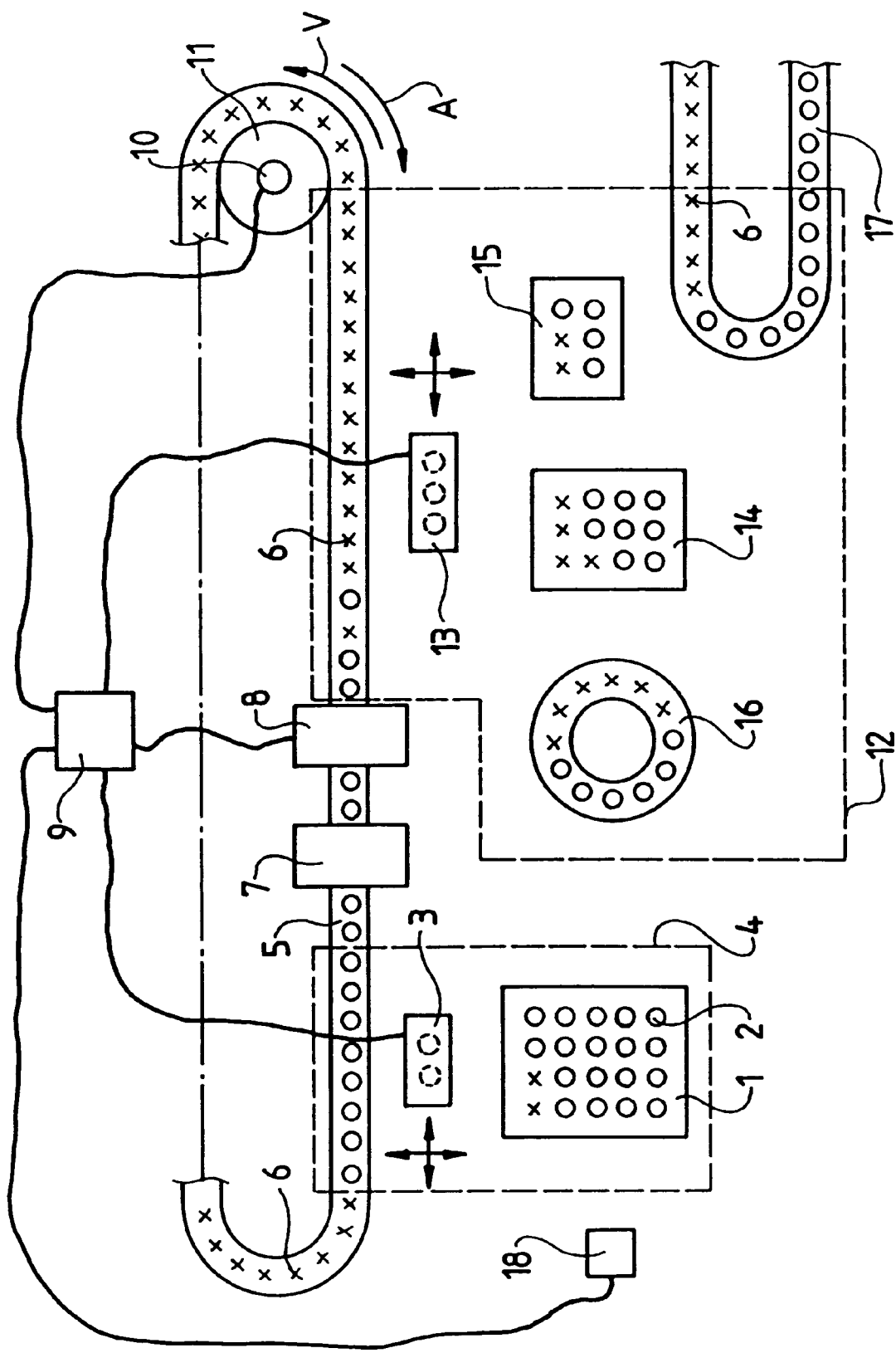

LABORATORY PRIMARY SAMPLE DISTRIBUTOR WITH ARCHIVING MODE

FIELD OF THE INVENTION

The invention relates to a laboratory primary sample distributor (hereafter primary distributor) with a source zone to feed coded receptacles containing samples which are delivered in input magazines, a conveyor belt to move the receptacles from the source zone through a reading system for reading the receptacle codes and into a destination zone where destination transport means are present with a transfer device to transfer the receptacles onto the conveyor belt, and a sorter device to remove the receptacles from the conveyor belt and to deposit them in the destination transport means, the primary distributor being controlled by a control unit.

BACKGROUND OF THE INVENTION

Typically, tubular receptacles are sent by physicians to clinical labs. These receptacles contain for instance blood, serum, urine or other body fluids to be tested, the tests being checked off by the physician on an accompanying tag or paper. Illustratively, the test may be for blood sugar, AIDS or a check on liver values or the like. Upon being received at the lab, the receptacles are first coded, for instance using stick-on labels, and the receptacle codes together with the test instructions are fed into a computer.

The receptacles are placed in input magazines. These may be racks receiving a row or rows of receptacles, trays receiving receptacles in substantially planar configuration, or also trays with racks resting on them.

Depending on test instructions, the receptacles must be conveyed to specific analyzers carrying out, for instance, blood-sugar or AIDS tests. Receptacles intended strictly only for particular analyzers are then moved on a destination transport means to such analyzers. Such a transportation means may be a tray manually moved to the analyzer, or a special, illustratively a circular magazine, also a conveyor belt sequentially moving the receptacles themselves, or receptacles placed in magazines, to the analyzer.

A primary distributor of this general type is known from German patent document 296 08 120 U1 and is used to distribute those receptacles arriving mixed in feed magazines to destination transport means.

After the primary distributor has fed the receptacles according to the desired test to the corresponding analyzers, the tests are performed. The test results are fed to the central computer in relation to the receptacle code, and the receptacles then exit the analyzer. Where called for, several tests are carried out on individual receptacles. In that case, the receptacles may be moved to a further analyzer.

Once all tests have been performed on a receptacle, such receptacles usually are archived, that is, stored or placed as such in an archive.

In conventional analyzers, the receptacles exit the analyzer in the same destination transport means on which they arrived. Standardized archive magazines are used, which allow suitable stacking in archive repositories, usually refrigerators, and which bear markings facilitating locating them and which also are preferred on other grounds, but mainly for economy, over the destination transport means, as regards placing the receptacles into the archive.

Typically, the transfer of the receptacles from the destination transport means into the archive magazines is manual and amounts to significant costs.

The known primary distributor of this general type can be conventionally used in an archive mode to place the receptacles into the archive. In this procedure, it moves in the ordinary direction of advance of its conveyor belt. The destination magazines returning from the analyzers are loaded in the source zone. The transfer device places the receptacles on the conveyor belt and the receptacles loaded onto it are removed in the destination zone by means of the sorter device and are placed in this destination zone into archive magazines.

In this manner the transfer of the receptacles into archive magazines can be mechanized in an economical manner.

However, the known archive mode incurs substantial drawbacks. Only standard magazines, for instance identical trays, can be used in the source zone. Accordingly, all analyzers must use the same destination trays. If the destination transport means is a conveyor belt, then receptacle transfer from this belt still must be performed manually. Furthermore, special magazines for individual analyzers, for instance round magazines, also preclude automated storage in the archive.

SUMMARY OF THE INVENTION

An object of the present invention is to provide a lab primary sample distributor having an archive mode allowing archiving from any destination transport means.

In accordance with the invention, the primary distributor will run backward in the archive mode. Destination transport means of different kinds returning from the analyzers can be unpacked by means of the very flexible sorter device. The much simpler transfer device is able to transfer the receptacles in very easy manner from the conveyor belt into the identical archive magazines, only a minor conversion of the feed magazines supplied by the feeding procedure into the archive magazines—which may be of a slightly different geometries—being required. As a result the full stream of receptacles can be stored entirely automatically in the archive even in a lab with highly individualistic equipment.

Advantageously, the system includes a magazine reading system for reading codes on archive magazines so that the archive magazines can be detected by means of deposited codings. The primary distributor moreover is able to read the codes on the receptacles and can determine the emplacement in the magazine when transferring the receptacles into the particular magazine. These data can be transmitted by the control system driving the primary distributor to a computer, for instance in the form of an archive tabulation, from which the information may be retrieved about which receptacle is located at which site in which archive magazine. In this manner the location of individual files in the archive, for instance a large refrigerator, is made easy.

BRIEF DESCRIPTION OF THE DRAWING

The invention is schematically shown in the drawing which is a top plan view of a primary distributor.

DESCRIPTION OF THE PREFERRED EMBODIMENT

The shown primary distributor first will be described when in its distribution mode.

Receptacles 2 of conventional tubular shape are delivered on an input magazine in the form of a tray 1. Already emptied receptacle seats of the tray 1 are denoted by crosses. A transfer device 3 is displaceable within a source zone 4 shown in dashed lines and wherein the tray 1 illustratively is set on a table, not shown. Transfer device 3 is designed to simultaneously move two receptacles. The seats of these receptacles are indicated in dashed form. Appropriately, the transfer device 3 is equipped for instance with a per se conventional x-y drive acting in the directions of the arrows. In this embodiment, the transfer device has two receptacle grippers shown in dashed lines and able to seize two adjacent receptacles at a time out of tray 1, to hold them and move them away.

The source zone 4, that is the displacement area of transfer device 3, is crossed by a conveyor belt 5 which, during the distribution mode, is driven in the direction of the arrow V. Conveyor belt 5 has receptacle seats 6 receiving the receptacles from transfer device 3. Empty receptacle seats of the conveyor belt are denoted by crosses.

Initially, conveyor belt 5 moves receptacles 2 in the direction of arrow V through apparatus 7 for opening the receptacles and, where called for, rotating them for code alignment. Next the receptacles move through a reading system 8 which reads the codes on containers 2 and communicates them through a signal line to a control unit 9 connected through the shown signal lines to the shown primary distributor's various components, said signal lines also including a control line with a drive motor 10 which, by means of a reversing wheel 11, drives the conveyor belt 5, and which is controlled in its drive direction by control unit 9.

The henceforth identified receptacles move toward the reading system 8 in the direction of arrow V into a destination zone 12 shown by dashed lines wherein they are removed from the belt by a sorter device 13 of a design similar to transfer device 3 and which in this illustrative embodiment comprises three seats, shown in dashed lines, to seize and hold receptacles.

Sorter device 13 is displaced by an x-y drive, not shown, within destination range 12 which encloses several destination transport means.

As destination transport means, the drawing shows a larger destination tray 14, a somewhat smaller destination tray 15, a round destination magazine 16, and a conveyor belt 17 to move the receptacles farther and which in the shown embodiment is designed to correspond to the conveyor belt 5, that is, being also fitted with receptacle seats 6. The destination trays illustratively are set on an table, not shown.

The different destination transport means 14, 15, 16 and 17 are used to move receptacles to specific analyzers, not shown. Trays 14, 15 and magazine 16 are manually moved to their particular analyzers. Conveyor belt 17 moving the receptacles farther passes through a directly connected analyzer. Empty seats of the destination transport means and of the continuing conveyor belt 17 are denoted by crosses.

Sensors, not shown, connected to control unit 9 detect the position and kind of transportation means set up in destination range 12, in such a manner that control unit 9 which is connected to sorter device 13 properly controls the sorter device to insert receptacles into receptacle seats of the destination transport means.

Once the receptacles have passed through their respective analyzers, they return from the analyzers on their particular destination transport means, that is, trays 14, 15, magazine 16 and where appropriate continuing conveyor belt 17, and then are transferred into standardized archive magazines suitable for storage, for instance, in a refrigerator. For that purpose and upon switching control unit 9, the shown primary distributor can be used in an archive mode.

First, the direction of motion of conveyor belt 5 is reversed to the direction of advance A, the returning and processed receptacles are kept ready, as shown in the FIGURE, together with their particular destination transport means, in destination zone 12. Destination trays 14, 15 are set up at their appropriate sites, including round destination magazine 16. Conveyor belt 17 on its return belt segment moves processed receptacles into destination zone 12.

Control unit 9 also drives sorter device 13 into reverse operation, namely to remove receptacles from destination transport means 14, 15, 16 and 17 and to deposit them on conveyor belt 5 into receptacle seats 6. Next, conveyor belt 5 moves the receptacles in the direction of advance A into source zone 4 where, instead of destination tray 1 being set up there during feed operation, now the archive magazines—which may correspond in their geometry substantially to that of the shown delivery tray 1—are set up.

Control unit 9 also drives transfer device 3 in the reverse procedure, that is to transfer incoming receptacles on conveyor belt 5 into the archive magazines standing in source zone 4.

Preferably, when control unit 9 is setting up an archive list, the receptacle codes are also read by reading system 8 in the archive mode, and codes deposited on the archive magazines are read using a magazine reading system 18 connected by a data line to control unit 9. Together with the control data of transfer device 3, the control unit can then feed an archive tabulation to the computer, said tabulation showing which receptacle in what magazine is located in what place.

What is claimed is:

1. A laboratory primary distributor comprising
   a source zone (4) to feed, in a distribution mode, coded receptacles (2) containing samples delivered in input magazines (1);
   a conveyor belt (5) to move said receptacles (2) in said distribution mode from said source zone (4) through a reading system (8) for reading receptacle codes (8) and into a destination zone (12);
   a transfer device (3) to transfer the receptacles (2) onto the conveyor belt (5) in said distribution mode; and
   a sorter device (13) to remove the receptacles (2) from the conveyor belt (5) and to deposit said receptacles into destination transport means (14, 15, 16, 17) in said distribution mode;
   a control unit (9) having an archive mode wherein said primary distributor is controlled so that said conveyor belt (5) runs backward relative to said distribution mode; and
   said sorter device (13) in said archive mode transfers receptacles (2) from the destination transport means (14, 15, 16, 17) onto said conveyor belt (5) and said transfer device (3) transfers receptacles (2) from said conveyor belt (5) into archive magazines (1).

2. A laboratory primary sample distributor according to claim 1 wherein a magazine reading system (18) reads codes on archive magazines (1) in said source zone (4).

* * * * *